(12) United States Patent
Mirkin et al.

(10) Patent No.: US 8,425,653 B2
(45) Date of Patent: Apr. 23, 2013

(54) PLASMON MEDIATED PHOTOINDUCED SYNTHESIS OF SILVER TRIANGULAR BIPYRAMIDS

(75) Inventors: Chad A. Mirkin, Wilmette, IL (US); Jian Zhang, Evanston, IL (US)

(73) Assignee: Northwestern University, Evanston, IL (US)

( * ) Notice: Subject to any disclaimer, the term of this patent is extended or adjusted under 35 U.S.C. 154(b) by 329 days.

(21) Appl. No.: 12/727,483

(22) Filed: Mar. 19, 2010

(65) Prior Publication Data

US 2010/0239675 A1    Sep. 23, 2010

Related U.S. Application Data

(60) Provisional application No. 61/162,117, filed on Mar. 20, 2009.

(51) Int. Cl.
*B22F 9/24* (2006.01)
*B82Y 40/00* (2006.01)

(52) U.S. Cl.
USPC ............................. 75/345; 75/371; 977/896

(58) Field of Classification Search ........................ None
See application file for complete search history.

(56) References Cited

U.S. PATENT DOCUMENTS

| | | | |
|---|---|---|---|
| 7,033,415 B2 * | 4/2006 | Mirkin et al. | 75/345 |
| 7,135,054 B2 * | 11/2006 | Jin et al. | 75/255 |
| 2005/0056118 A1 * | 3/2005 | Xia et al. | 75/330 |
| 2008/0003130 A1 * | 1/2008 | Xia et al. | 420/501 |

OTHER PUBLICATIONS

Bastys et al., Formation of silver nanoprisms with surface plasmons at communication wavelenths, *Adv. Funct. Mater.*, 16:766-73 (2006).
Burda et al., Chemistry and properties of nanocrystals of different shapes, *Chem. Rev.*, 105:1025-102 (2005).
Daniel et al., Gold nanoparticles: assembly, supramolecular chemistry, quantum-size-related properties, and applications toward biology, catalysis, and nanotechnology, *Chem. Rev.*, 104:293-346 (2004).
Eustis et al., Why gold nanoparticles are more precious than pretty gold: noble metal surface plasmon resonance and its enhancement of the radiative and nonradiative properties of nanocrystals of different shapes, *Chem. Soc. Rev.*, 35:209-17 (2006).
Hao et al., Synthesis of silver nanodisks using polystyrene mesospheres as templates, *J. Am. Chem. Soc.*, 124:15182-3 (2002).
Jin et al., Controlling anisotropic nanoparticle growth through plasmon excitation. *Nature*, 425:487-90 (2003).
Jin et al., Photoinduced conversion of silver nanospheres to nanoprisms, *Science*, 294:1901-3 (2001).
K M et al., Platonic gold nanocrystals, *Angew. Chem. Ed. Engl.*, 43:3673-7 (2004).
Lal et al., Nano-optics from sensing to waveguiding, *Nat. Photonics*, 1:641-8 (2007).
Liu et al., Mechanisms of silver(I)-assisted growth of gold nanorods and bipyramids, *J. Phys. Chem. B*, 109:22192-200 (2005).

(Continued)

*Primary Examiner* — George Wyszomierski
(74) *Attorney, Agent, or Firm* — Marshall, Gerstein & Borun LLP

(57) ABSTRACT

A method of preparing silver triangular bipyramids having a high shape selectivity and low edge length variation is disclosed. Also disclosed are silver triangular bipyramids prepared by this method.

15 Claims, 7 Drawing Sheets

OTHER PUBLICATIONS

McEachran et al., Direct structural transformation of silver platelets into right bipyramids and twinned cube nanoparticles: morphology governed by defects, *Chem. Commun. (Camb).*, Nov. 30:5737-9 (2008).

Metraux et al., Rapid thermal synthesis of silver nanoprisms with chemically tailorable thickness, *Adv. Mater.*, 17:412-5 (2005).

Millstone et al., Controlling the edge length of gold nanoprisms via a seed-mediated approach, *Adv. Funct. Mater.*, 16:1209-14 (2006).

Nie et al., Probing single molecules and single nanoparticles by surface-enhanced raman scattering, *Science*, 275:1102-6 (1997).

Pietrobon et al., Photochemical synthesis of monodisperse size-controlled silver decahedral nanoparticles and their remarkable optical properties, *Chem. Mater.*, 20:5186-90 (2008).

Rocha et al., Formation kinetics of silver triangular nanoplates, *J. Phys. Chem. C*, 111:2885-91 (2007).

Rosi et al., Nanostructures in biodiagnostics, *Chem. Rev.*, 105:1547-62 (2005).

Seo et al., Shape adjustment between multiply twinned and single-crystalline polyhedral gold nanocrystals: decahedra, icosahedra, and truncated tetrahedra, *J. Phys. Chem. C.*, 112:2469-75 (2008).

Seo et al., Polyhedral gold nanocrystals with O h symmetry: from octahedra to cubes, *J. Am. Chem. Soc.*, 128:14863-70 (2006).

Sun et al., Crystalline silver nanowires by soft solution processing, *Nano Lett.*, 2:165-8 (2002).

Sun et al., Shape-controlled synthesis of gold and silver nanoparticles, *Science*, 298:2176-9 (2002).

Thaxton et al., Templated spherical high density lipoprotein nanoparticles, *J. Am. Chem. Soc.*, 131:1384-5 (2009).

Wiley et al., Shape-controlled synthesis of silver and gold nanostructures, *MRS Bulletin*, 30:356-61 (2005).

Wiley et al., Right bipyramids of silver: a new shape derived from single twinned seeds, *Nano Lett.*, 6:765-8 (2006).

Wiley et al., Synthesis and optical properties of silver nanobars and nanorice, *Nano Lett.*, 7:1032-6 (2007).

Wu et al., Photovoltage mechanism for room light conversion of citrate stabilized silver nanocrystal seeds to large nanoprisms, *J. Am. Chem. Soc.*, 130:9500-6 (2008).

Xue et al., Mechanistic study of photomediated triangular silver nanoprism growth, *J. Am. Chem. Soc.*, 130:8337-44 (2008).

Xue et al., pH-switchable silver nanoprism growth pathways, *Angew. Chem. Int. Ed. Engl.*, 46:2036-8 (2007).

Yang et al., Discrete dipole approximation for calculating extinction and Raman intensities for small particles with arbitrary shapes, *J. Chem. Phys.*, 103:869-75 (1995).

Yu et al., Hydrothermal-induced assembly of colloidal silver spheres into various nanoparticles on the basis of HTAB-modified silver mirror reaction, *J. Phys. Chem. B*, 109:5497-503 (2005).

Zhao et al., Methods for describing the electromagnetic properties of silver and gold nanoparticles, *Acc. Chem. Res.*, 41:1710-20 (2008).

Zheng et al., Laser-induced growth of monodisperse silver nanoparticles with tunable surface plasmon resonance properties and a wavelength self-limiting effect, *J. Phys. Chem. C*, 111:14962-7 (2007).

Zhou et al., Growth of tetrahedral silver nanocrystals in aqueous solution and their SERS enhancement, *Langmuir*, 24:10407-13 (2008).

\* cited by examiner

PLASMON MEDIATED PHOTOINDUCED SYNTHESIS OF SILVER TRIANGULAR BIPYRAMIDS

CROSS-REFERENCE TO RELATED APPLICATIONS

This application claims the benefit of U.S. Provisional Application Ser. No. 61/162,117, filed Mar. 20, 2009, which is incorporated by reference in its entirety herein.

STATEMENT OF GOVERNMENT INTEREST

This invention was made with U.S. government support under National Science Foundation (NSF-MRSEC) Grant No. DMR-0520513. The government has certain rights in this invention.

BACKGROUND

Synthetic methods have been developed for producing a wide variety of nanostructures that differ in size, shape, and composition. Methods now exist for preparing nonspherical, monodisperse samples of Au and Ag triangular prisms,(1-5) cubes,(6,7) wires,(8) bars,(9) tetrahedra,(7,10) octahedra,(11) decahedra,(12,13) bipyramids,(14) and disks.(15) Synthetic control over particle shape allows one to chemically tailor the optical, electric, magnetic, and catalytic properties of such structures, making them useful for many applications, including biological diagnostics,(16) therapeutics,(17) catalysis,(18,19) and optics.(20,21)

One of the most controllable synthetic methods for making anisotropic nanostructures involves the photochemical conversion of silver (Ag) spheres into triangular prisms.(1) With this synthetic method, the growth of the silver nanoprisms can be modulated through a combination of photoexcitation and pH control,(2,22) and the resulting edge length of the nanoprisms can be controlled by excitation wavelength. The prisms grow via a photo-mediated process until their plasmon resonances are red-shifted from the excitation wavelength. This method has been widely used to synthesize silver nanoprisms and other related structures (e.g., nanodisks or truncated prisms).(23-26) In addition, even more exotic structures, such as decahedra and tetrahedra can be realized through plasmon-mediated syntheses, although wavelength driven size control has not been demonstrated with these particle shapes.(10,13)

The use of plasmon excitation to control nanostructure growth has significant advantages over thermal methods. Most notably, it allows one to control particle size and reaction rate simply through choice of excitation source and wavelength. The photogeneration of triangular silver prisms is one of the excellent examples of the utility of such methods. Indeed, one can generate equilateral triangular prisms with a fixed thickness and an edge length which is tunable over the 40 to 120 nm range simply by choice of excitation wavelength and pH. This system, although impressive, is the only example to date where excitation wavelength driven particle size control has been demonstrated.

SUMMARY

Disclosed herein are silver triangular bipyramids and methods of making them. Thus, in one aspect, disclosed herein is a method of preparing silver triangular bipyramids comprising irradiating a mixture comprising a silver salt, a reducing agent, a separation agent, and a base with light at a selected band of wavelengths for a time sufficient to form the silver triangular bipyramids having an a edge length and a b edge length, wherein the silver salt comprises a silver ion, a molar ratio of separation agent to silver ion is at least 1:1, and the selected band of wavelengths of the light correlates to the a edge length of the silver triangular bipyramid. The method can provide at least 85% or greater than 95% shape selectivity of triangular bipyramids. In some cases, the method provides silver triangular bipyramids having a variation in the a or b edge length of less than 15%, or less than 10%. In various cases, the molar ratio of separation agent to silver ion is 1:1 to about 1:4.

In various embodiments, the silver salt comprises silver nitrate. In some cases, the separation agent comprises bis(p-sulphonatophenyl)phenylphosphine dehydrate dipotassium (BSPP). In various cases, the reducing agent comprises citric acid or a salt thereof, such as sodium citrate. In some cases, the base is an inorganic base, such as sodium hydroxide.

In some specific cases, the mixture being irradiated consists essentially of a silver salt, a reducing agent, a separation agent, and a base. In more specific cases, the silver salt of this mixture is silver nitrate; the reducing agent is sodium citrate; the separation agent is BSPP; and/or the base is an inorganic base.

In some embodiments, the selected band of wavelengths has a full width at half maximum (FWHM) of 50 nm or less, or a FWHM of about 40 nm. In some specific cases, the selected band of wavelengths is selected from the group consisting of 500±20 nm, 550±20 nm, 600±20 nm, and 650±20 nm. In various cases, the light has a power intensity of about 0.1 to about 1 W, or about 0.3 to about 0.5 W. In some cases, the mixture is irradiated with the selected band of wavelengths for about 3 to about 8 hours.

In yet another aspect, disclosed herein are compositions of silver particles, wherein at least 90% of the silver particles are bipyramids. In some embodiments, the triangular bipyramids have a variation in an a or b edge length of less than 10%. In various cases, the triangular bipyramids have a twinned crystal structure. In some specific cases, the a edge length of the triangular bipyramids are about 106±9 nm, about 131±12 nm, about 165±12 nm, or about 191±8 nm. In various cases, the triangular bipyramids have all tips truncated.

BRIEF DESCRIPTION OF THE DRAWINGS

FIG. 1A is a perspective view; 1B a side view; and 1C a top view, when the right pyramid is placed on a planar substrate.

DETAILED DESCRIPTION

Figure 1:
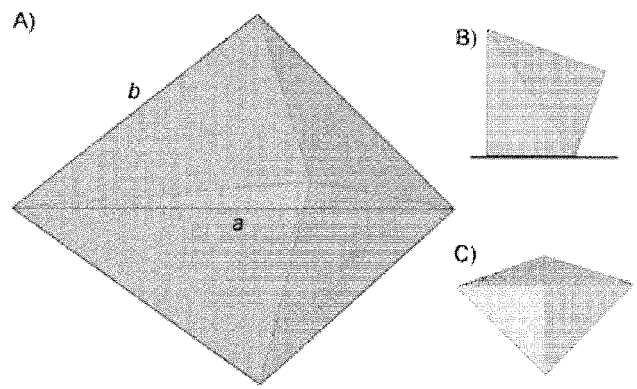
FIG. 1 shows a schematic of the silver triangular bipyramids prepared by the disclosed methods.

Disclosed herein are methods of preparing silver right triangular bipyramids using a new plasmon-mediated particle growth method (FIG. 1). FIG. 1 shows a schematic of a right triangular bipyramid, where 1A is a perspective view; 1B is a side view and 1C is a top view when the right pyramid is placed on a planar substrate. Silver right triangular bipyramids are structurally related to triangular prisms(27) and consist of two right tetrahedra symmetrically joined base-to-base (FIG. 1A). Their sharp vertices are particularly promising for applications related to surface-enhanced Raman scattering (SERS)(28) and plasmonics in general. Excitation wavelength in this system can be used to control the dimensions of the two right pyramids forming each particle.

Silver right triangular bipyramids have been synthesized by a thermal polyol synthesis, but the thermal method yielded only 80% bipyramids and 20% cubes.(27) The photochemical method described herein allows one to prepare silver triangular bipyramids which have greater than 85% shape selectivity (e.g., less than 15% of the material is other than the desired triangular bipyramids) and/or with less than 15% variation in edge length. In some cases, the silver triangular bipyramids have greater than 86%, greater than 87%, greater than 88%, greater than 89%, greater than 90%, greater than 91%, greater than 92%, greater than 93%, greater than 94%, greater than 95% shape selectivity. In various cases, the silver triangular bipyramids have less than 14%, less than 13%, less than 12%, less than 11%, less than 10%, or less than 9% variation in edge length.

The purity of the silver triangular bipyramids produced by the method disclosed herein can be indicated by characterization of the shape selectivity and/or the variation in the edge length. Thus, a description of the shape selectivity and/or edge length can reflect the purity of the triangular bipyramids produced by the method and indicate that shapes other than triangular bipyramids may be produced as a byproduct of the method.

Theoretical calculations have been used to assign the different plasmon excitation bands from the extinction spectra of the bipyramids, and the correlation between experimentally measured UV-vis spectra and calculated spectra confirm the monodispersity of the bipyramids prepared by the disclosed method.

A typical photoinduced synthesis is performed by irradiating an aqueous solution of a silver salt (e.g., $AgNO_3$), a reducing agent (e.g., citric acid), a separation agent (e.g., bis(p-sulfonatophenyl) phenylphosphine dihydrate dipotassium salt (BSPP)), and a base (e.g., NaOH).

Other non-limiting examples of silver salts that can be used include silver chloride, silver acetate, silver sulfate, silver perchlorate, silver nitrate, and mixtures thereof. Contemplated concentrations of silver salt include about 0.1 to about 3 mM. Other contemplated concentrations include about 0.15 to about 2 mM, about 0.2 to about 1 mM, and about 0.25 to about 0.5 mM.

Other examples of reducing agents that can be used include ascorbic acid, ascorbic acid salts (e.g., sodium ascorbate), citric acid, citric acid salts (e.g., (mono)sodium citrate), sodium triacetoxy borohydride, diisobutylaluminum hydride, lithium aluminum hydride, potassium tri-sec-butylborohydride, potassium triethylborohydride, sodium tri-sec-butylborohydride, lithium triethylborohydride, lithium tri-sec-butylborohydride, methyl oxazaborolidine, diisopinocampheylchloroborane, methoxydiethylborane, dibutylboron triflate, dicyclohexylboron triflate, dicyclohexylchloroborane, borane-tetrahydrofuran complex, dimethylsulfide borane, diethylaniline borane, tert-butylamine borane, morpholine borane, dimethylamine borane, triethylamine borane, pyridine borane, and mixtures thereof. Contemplated concentrations for the reducing agent (e.g., sodium citrate) are from about 0.05 to 15 mM. Other contemplated concentrations for the reducing agent include about 0.3 to about 7 mM, about 0.5 to about 5 mM, and about 0.6 to about 3.5 mM.

As used herein, "separation agent" refers to an additive capable of preventing nanoprism agglomeration. One or more separation agent can be added to the admixture. In some embodiments, the separation agent comprises bis(p-sulphonatophenyl)phenylphosphine dehydrate dipotassium (BSPP). Additional and nonlimiting examples of ligands include polyvinylpyrrolidine, sodium poly(acetate), polyethyleneimine, ethylenediaminetetraacetate salts, and related polyamino carboxylic acid salts, diethylenetriaminepentaacetic acid, N-hydroxyethylethylenediaminetriaacetic acid, nitrilotriacetic acid, and mixtures thereof. Contemplated concentrations for the separation agent are from about 0.01 to about 2 mM. Other contemplated concentrations for the separation agent include 0.1 to 1 mM, 0.15 to 0.75 mM, and 0.2 to 0.5 mM.

The molar ratio of separation agent to reducing agent is about 1:3 to about 1:7. Specific contemplated ratios include 1:3, 1:3.5, 1:4, 1:4.5, 1:5, 1:5.5, 1:6, 1:6.5, and 1.7. For example, a molar ratio of separation agent to reducing agent of 1:3 indicates that for every mole (or mmol) of separation agent, three mole (or mmol) of reducing agent is present.

The molar ratio of separation agent to silver ion (from the silver salt) is at least 1:1. Specific contemplated ratios include 1:1, 1:1.5, 1:2, 1:2.5, 1:3, and 1:3.5. Other contemplated ranges for the molar ratio of separation agent to silver ion include about 1:1 to about 1:4, about 1:1 to about 1:3, and about 1:1 to about 1:2. The high concentration of the silver ions in the reaction mixture, without going through an intermediate silver nanoparticle allows for formation of the silver triangular bipyramid instead of other morphologies, such as a triangular nanoprism, as disclosed in U.S. Pat. No. 7,033,415, which is incorporated by reference herein in its entirety.

The mixture further contains a base. The base can be an inorganic (e.g., alkali or alkaline earth metal) base, an organic base (e.g., an amine), or a mixture thereof. Specifically contemplated bases include sodium hydroxide, lithium hydroxide, potassium hydroxide, cesium hydroxide, magnesium hydroxide, calcium hydroxide, barium hydroxide, a trialkyl amine (e.g., triethyl amine, diisopropylethyl amine), or mixtures thereof. Contemplated concentrations of the base include about 0.1 to about 10 mM, about 0.2 to about 7 mM, about 0.5 to about 5 mM, and about 1 to about 5 mM.

The mixture is irradiated with a light source for a time sufficient to form the triangular bipyramids. The mixture is typically irradiated at least 1 hour, but can be irradiated for 2 to 10 hours, 3 to 9 hours, or 4 to 8 hours.

Figure 3B:
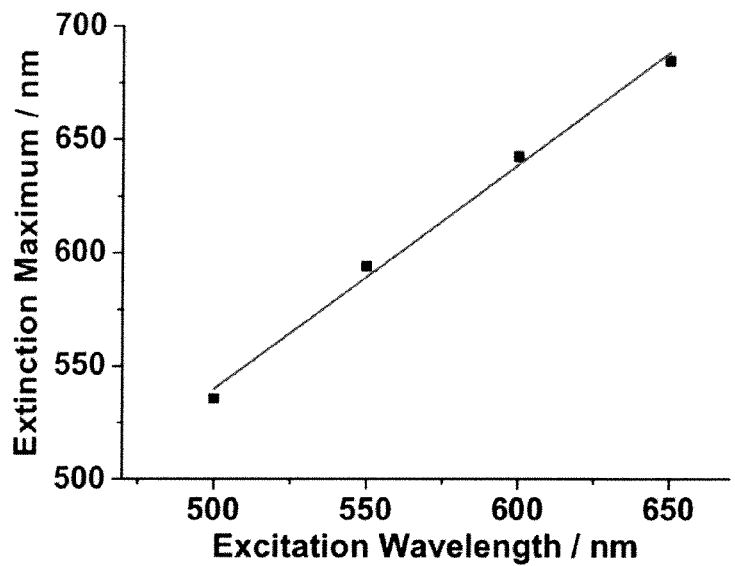
Figure 4A:
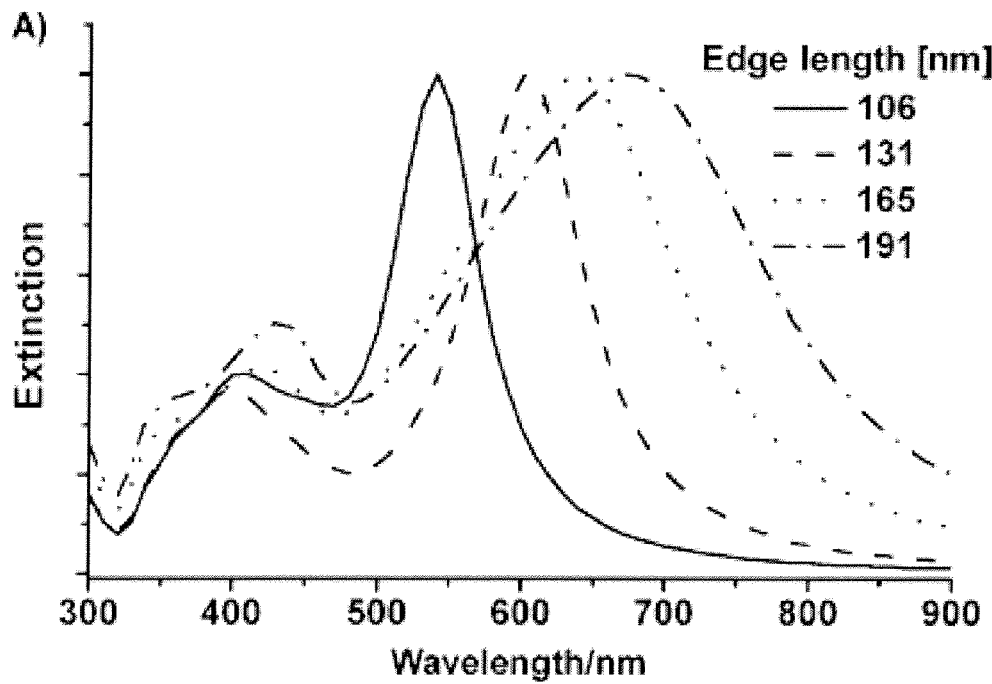
FIG. 4 shows A) normalized discrete dipole approximation (DDA) simulations of the orientation averaged UV-vis-NIR spectra of right triangular bipyramids with four different edge lengths in water; and B) DDA simulations of the orientation averaged extinction efficiency spectra of right triangular bipyramid with different truncation.

The power density of the light irradiating the mixture can be from about 0.1 to about 1 Watt (W), about 0.2 to about 0.7 W, or about 0.3 to 0.5 W. The irradiation can be performed by any light source that allows for selection of the wavelengths. In some cases, the light source only emits light having the preselected wavelengths. Alternatively, the light source comprises an optical bandpass filter. An optical bandpass filter allows for control over the desired excitation wavelength range. The optical bandpass allows passage of a selected band of wavelengths of light from the light source to the mixture. Some contemplated bands of wavelengths include a band of about 40 nm centered around a selected wavelength (e.g., 500±20 nm, 550±20 nm, 600±20 nm, 650±20 nm). In some cases, the band of wavelengths are indicated as a full width at half max (FWHM) value of the wavelengths of light irradiating the mixture. The FWHM of the band can be about 10 nm, about 20 nm, about 30 nm, about 40 nm, or about 50 nm. The selection of the band of wavelengths impacts the size (edge length) of the resulting silver triangular bipyramids. Shorter wavelengths result in shorter edge lengths, while increasing the wavelengths for irradiation increases the edge length. This correlation can be seen in the plot of FIGS. 3B and 4A, showing the direct correlation between excitation wavelength and $\lambda_{max}$ and the direct correlation between $\lambda_{max}$ and edge length.

The mixture is excitation by the selected wavelengths, which can excite plasmon resonance(s). As the triangular bipyramids grow, the plasmon resonance(s) shift. The growth of the triangular bipyramids can continue until there is little or no overlap of the plasmon resonance(s) with the excitation wavelengths.

After 30 minutes, the reaction solution turned from colorless to light yellow. With continued irradiation (1 h), the color of the solution continued to change, with the final solution color obtained depending upon the excitation wavelength used (FIG. 1). For example, when the solution was irradiated with 500±20 nm light, a red solution was obtained with a UV-vis band at $\lambda_{max}$=535 nm. Similarly, if the solution was irradiated with 550±20 nm light, a blue solution was obtained with a UV-vis band centered at $\lambda_{max}$=590 nm.

Figure 2:
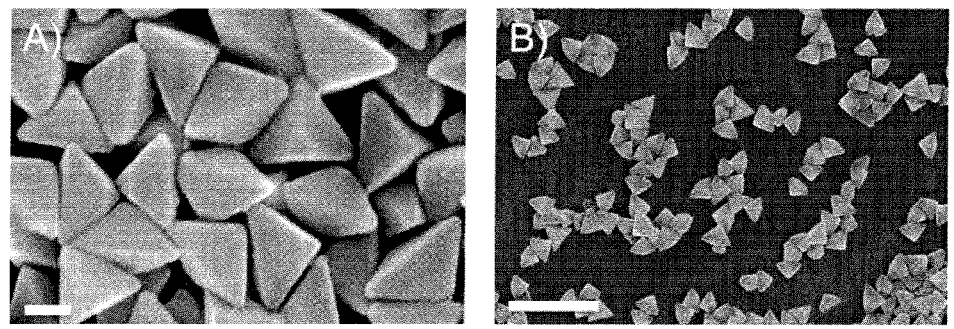
FIG. 2 shows A) a high magnification scanning electron microscopy (SEM) image of the right triangular bipyramids (scale bar 60 nm) and B) a wider, lower resolution view of the same sample (scale bar 500 nm). These structures were generated with the band pass filter centered at 550±20 nm.

SEM images (FIG. 2) of the nanoparticles prepared by light having an excitation wavelength centered around 550 nm show that they are highly monodisperse right triangular bipyramids. Note that the bipyramid is a three dimensional object, with one of its six facets sitting on the substrate (Scheme 1C). Only two dimensional projections of such structures can be observed by SEM and TEM, and therefore the triangular bipyramids appear as irregular tetragons or triangles.[29,30] Each structure has six right isosceles triangular faces with equilateral triangle as a base (Scheme 1A). There are two different edge lengths associated with the bipyramids, denoted as edge length a and b, where a=$\sqrt{2}$b. For the sample produced with the band pass filter centered at 550 nm, a and b were determined to be 131±12 nm and 93±9 nm, respectively, from SEM images. The ratio between these two edge lengths (1.41) is consistent with the expected value of $\sqrt{2}$. There are overall five vertices in one bipyramid. Three vertices in the plane of equilateral triangular base are defined as longitudinal vertices, and the other two vertices are defined as transverse vertices. SEM images indicate that the vertices of the right bipyramids are slightly truncated (FIG. 2A). For example, for bipyramids made from irradiation at 550 nm, truncations of the three longitudinal and two transverse tips are 20±5 nm and 30±7 nm, respectively. Truncation greatly affects the surface plasmon resonance of these metallic nanoparticles, discussed in greater detail below.

The particle dimensions are highly tailorable through choice of excitation wavelength with 500±20 nm, 550±20 nm, 600±20 nm, and 650±20 nm sources yielding monodisperse samples of bipyramids with edge lengths (a) of 106±9 nm, 131±12 nm, 165±12 nm, and 191±8 nm, respectively. In general, the edge length of the right bipyramids increases as the excitation wavelength increases over this wavelength range. Thus, the edge length of the resulting bipyramids can be tailored by choosing a corresponding irradiation wavelength.

Figure 3A:
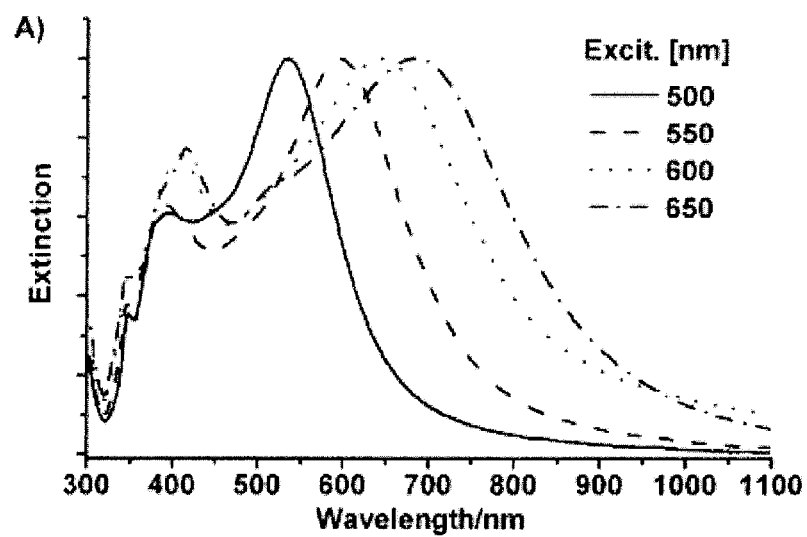
FIG. 3 shows A) normalized extinction spectra of the aqueous solution of silver triangular bipyramids prepared with excitation at 500±20 nm, 550±20 nm, 600±20 nm, and 650±20 nm respectively, and B) a plot of extinction maximum of different bipyramids vs. different excitation wavelength.

The ultraviolet-visible-near-infrared (UV-vis-NIR) spectra of the colloidal suspensions of particles formed from this photomediated method were also measured (FIG. 3A). The UV-vis-NIR spectra of the colloidal suspensions of each of the four different sized bipyramids, exhibit three distinct bands. Two are centered around 355 and 400 nm, and they are similar in all four spectra. The third band is at longer wavelength (ranging from 530 nm to 730 nm) and is highly dependent upon the size of the bipyramids. In general, as the particle increases in size, this band red shifts and is at slightly longer wavelength than the excitation source. There is a linear correlation between excitation wavelength and the maximum wavelength of surface plasmon resonance band of bipyramids (FIG. 3B). This result indicates that the formation of the triangular bipyramids is a plasmon-mediated process. These results are significant because they not only provide a simple method to precisely control the edge length of silver bipyramids, but also indicate that the surface plasmon resonance can indeed be utilized as a tool to control nanoparticle size and shape in structures other than triangular prisms.[1,2]

The optical properties of the triangular bipyramids, including light absorption and scattering, as well as surface-enhanced Raman specstroscopy, should be influenced by their structural anisotropy, which is significantly different from both small spherical nanoparticles and triangular nanoprisms. As predicted by Mie theory, the larger anisotropic particles can exhibit multiple surface plasmon bands, including dipole, quadrupole and higher multipole plasmon excitation. To characterize and understand the extinction spectra shown in FIG. 3, extinction spectra were calculated using the discrete dipole approximation (DDA) method.[31] The DDA method, which numerically solves Maxwell's equations for particles with arbitrary shapes, has been previously applied to various nanoparticles.[32] The edge length of the bipyramids and the tip truncation length are measured based on average structures found in the SEM images. The extinction spectra from the DDA calculations are plotted in FIG. 4A for the bipyramids with the edges a taken to be 106 nm, 131, nm, 165 nm, and 191 nm, respectively. The agreement between experiment and calculation provides additional evidence of the high monodispersity of the bipyramids. Slight broadening of the bands in the experimental spectra can be attributed to the edge length distribution (4% to 9%) of the bipyramids.

Figure 4B:
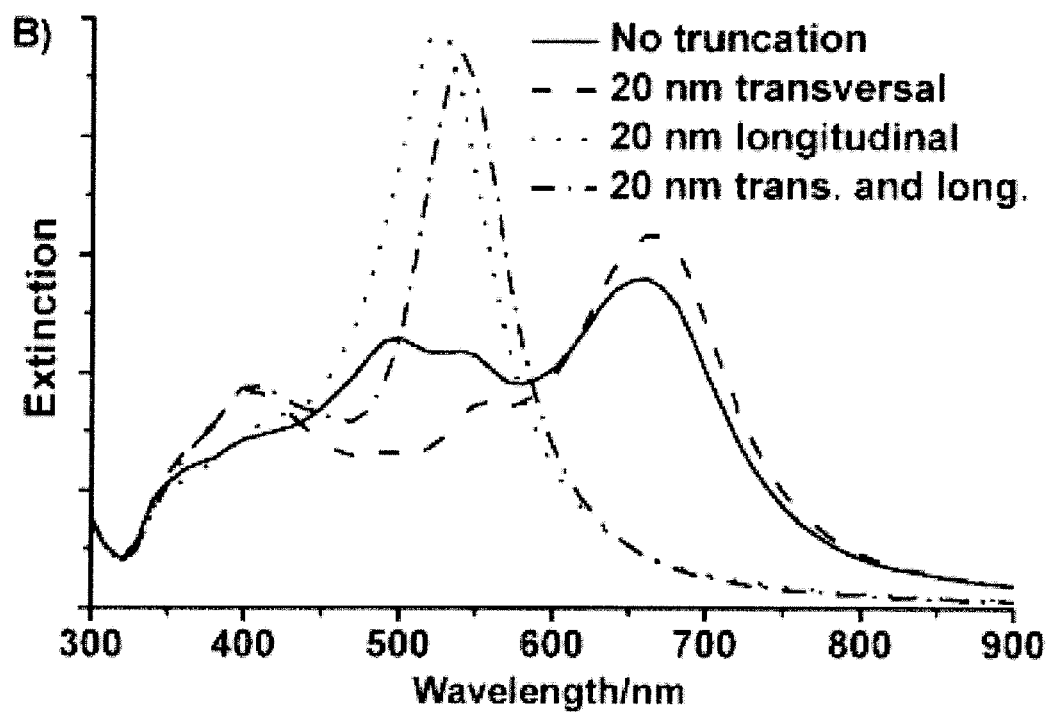

The effect of tip truncation was studied to identify the important features in the extinction spectra of the bipyramids and to assign different bands. This effect was studied by comparing the calculated extinction spectra for a perfect right bipyramid with those bipyramids with truncation. Based on a calculation for a perfect triangular bipyramid with an a edge length of 106 nm, the spectrum of the perfect bipyramid is significantly different from that of the truncated bipyramid (FIG. 4B). When only the two transverse tips are truncated, the band around 500 nm blue shifts to 400 nm and there is almost no change for the band at 670 nm. When the other three longitudinal tips are truncated, the 670 nm band blue-shifts to 525 nm. When all the five tips of the bipyramid are truncated, both bands blue-shift, and the resulting spectra match well with the experimental one. From these comparisons, the calculated spectra shown above are an overall effect of the tip truncation on both longitudinal and transverse orientation. These comparisons also indicate that the bands around 400 nm and 530 nm in the measured spectrum is attributed to the transverse and longitudinal plasmon resonance modes of the bipyramid, respectively.

Figure 5:
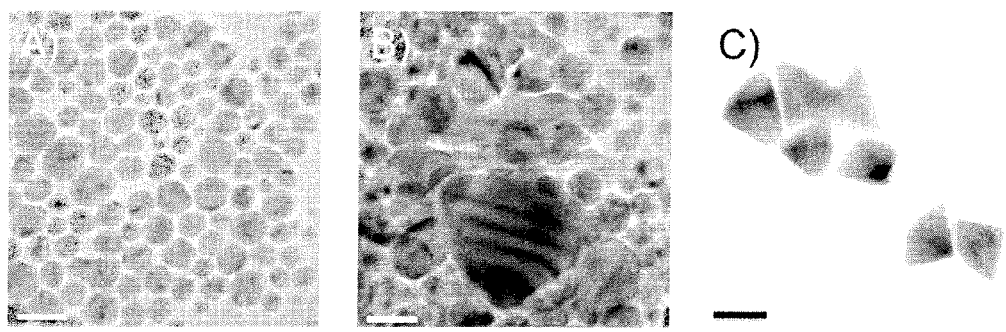
FIG. 5 shows tunneling electrom microscopy (TEM) images of a sample taken by stopping the reaction after about 1 hour (5A, scale bar 20 nm), 2 hours (5B, scale bar 20 nm), and 8 hours (5C, scale bar 100 nm).

Other experiments were performed to gain insight into the structure and the mechanistic basis behind the bipyramid synthesis. First, tunneling electron microscopy (TEM) was used to investigate the reaction process by studying the formed nanoparticles at different reaction time. Three distinctive stages were identified (FIG. 5). Within one hour of irradiation, spherical silver nanocrystals form from silver salt (e.g., $AgNO_3$) in the presence of a reducing agent (sodium citrate) under the irradiation of visible light, which presumably is a thermal process. Once the spherical silver particles form, the reaction is driven by the plasmon excitation, similar to the photoinduced silver nanoprisms synthesis. During the second stage, the spherical nanocrystals enlarge and some small triangular bipyramids appear, which can be identified in the TEM images taken from after 2 hours. In the last termination stage, more $Ag^+$ ions are reduced and deposited on the small bipyramids and form the final bipyramids.

Figure 6A:
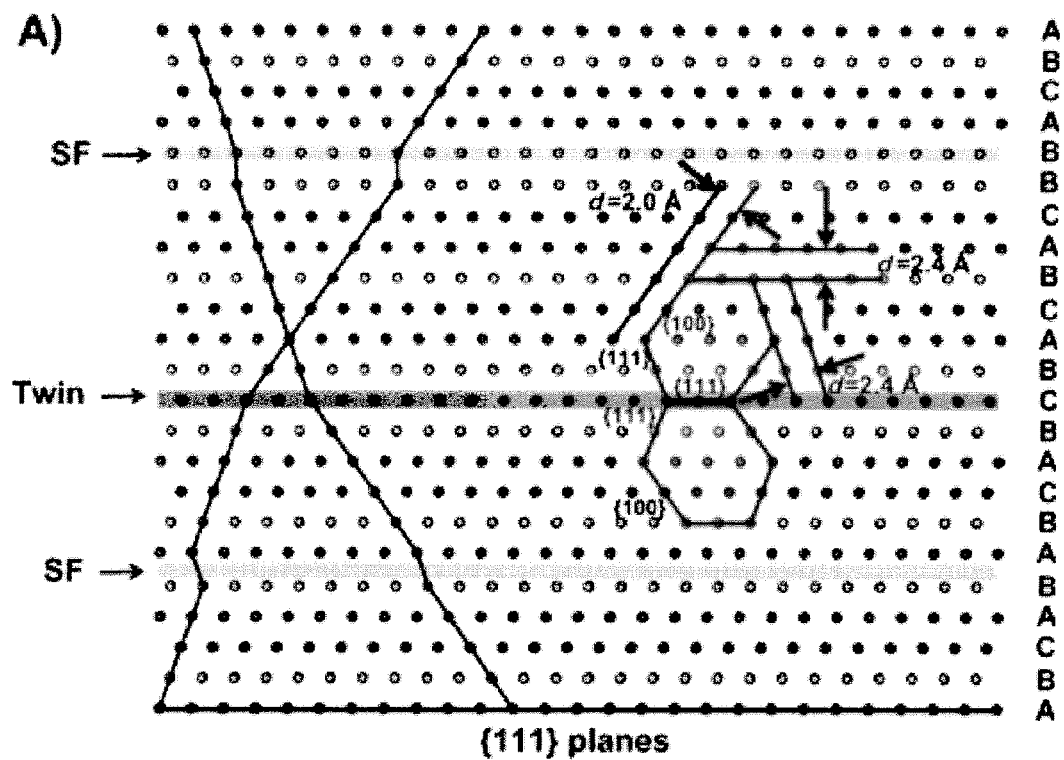
FIG. 6 shows A) a scheme showing a twin plane and stacking faults along {111} plane in a fcc crystal; B and C) high-resolution TEM (HR-TEM) images of a seed (5B, scale bar 2 nm) and a small bipyramid (6C, scale bar 4 nm; inset: zoom out view of this bipyramid, scale bar, 20 nm) showing multiple planar twinned planes along with stacking faults when the reaction was stopped at one hour and two hours, respectively (excitation wavelength 550±20 nm).
Figure 6B:
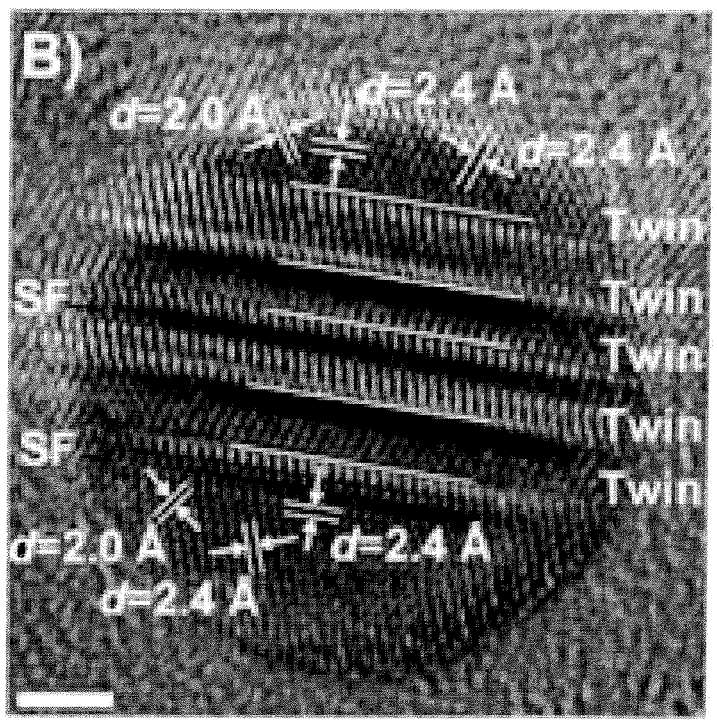
Figure 6C:
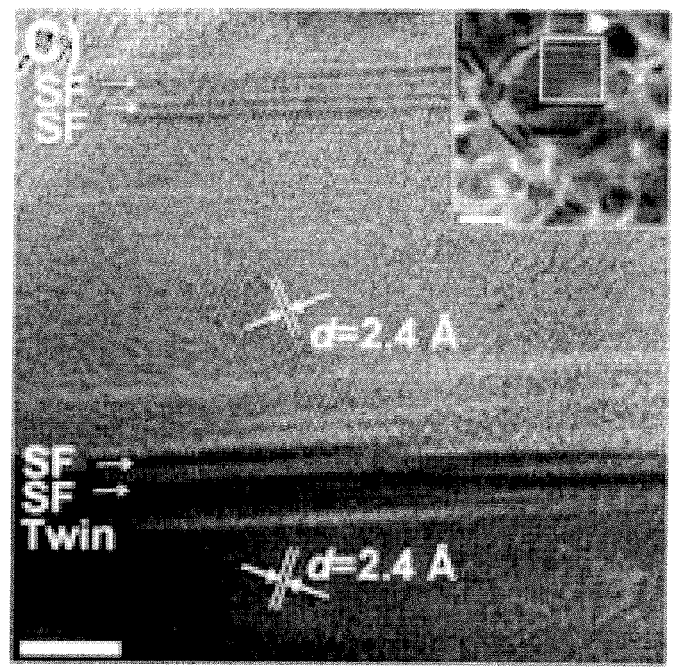
Figure 11:
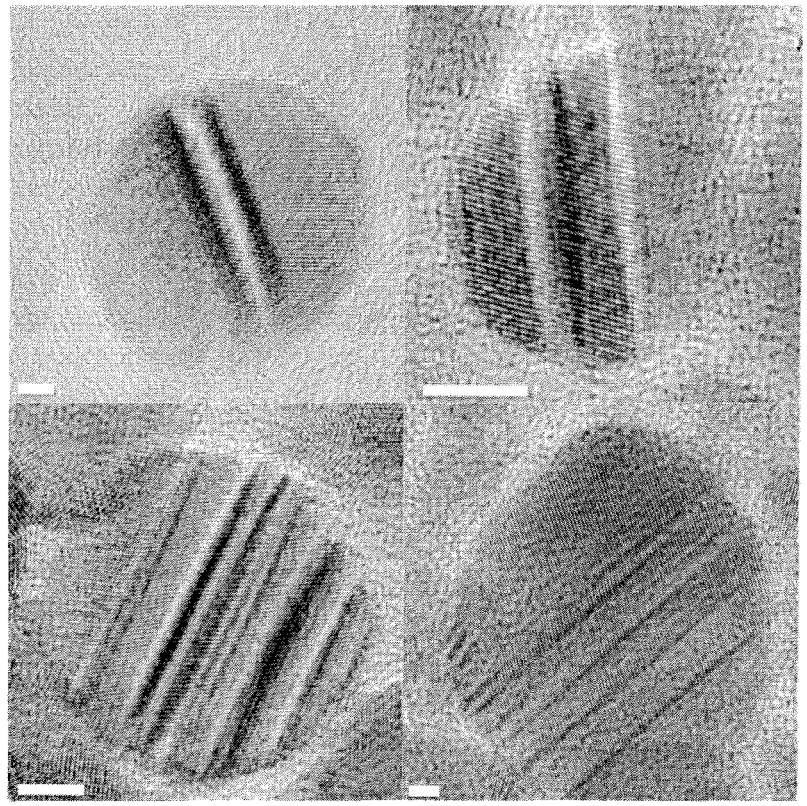
FIG. 11 shows HR-TEM images of seeds (scale bar 2 nm) showing planar twinned planes and stacking faults when the reaction was stopped at one hour.

For silver nanoprisms, the planar stacking faults (SF) and twin planes have been identified and are considered as an important factor to explain nanoprism formation. Silver nanocrystals formed at different stages in the bipyramid synthesis by using high resolution electron microscopy (HREM). For noble metal face-center-cubic structures, the twin planes and stacking defaults usually happen on the {111} planes. The best orientation for one to visualize these defects is along the <110> zone axis when the {111} planes are edge on. At this orientation, one {100} and two {111} planes are aligned with the electron beam, which is perpendicular to the {110} plane. FIG. 6A is a schematic representation of the atoms in a crystal in this orientation, showing one twin plane and two stacking faults. The {110} plane of the crystal is within the plane of the scheme, and the two {111} planes and one {100} plane can be identified; the spacing for {111} planes and {100} planes are 2.4 Å and 2.0 Å respectively. The crystal structure of the seeds was studied by stopping the photoinduced reaction after one hour of irradiation, and the intermediate bipyramids by stopping the reaction after two hours of irradiation. For the one-hour sample, nanoparticles with twinned planes, mainly multiple planar twinned defects can readily be found (FIG. 6B and FIG. 11). In the particular crystal shown in FIG. 6B, there are five twin planes and two stacking faults. The different spacings between fringes were measured as 2.4 Å for {111} planes and 2.0 Å for {100} planes, which are consistent with the expected values. FIG. 5C shows a HRTEM image of an intermediate small bipyramid, whose orientation is a little bit away from the <110> zone axis. In the image, the fringes for {111} planes can still be seen, which has 2.4 Å spacing, and one twin and four stacking faults interfaces can then be identified.

Figure 7:
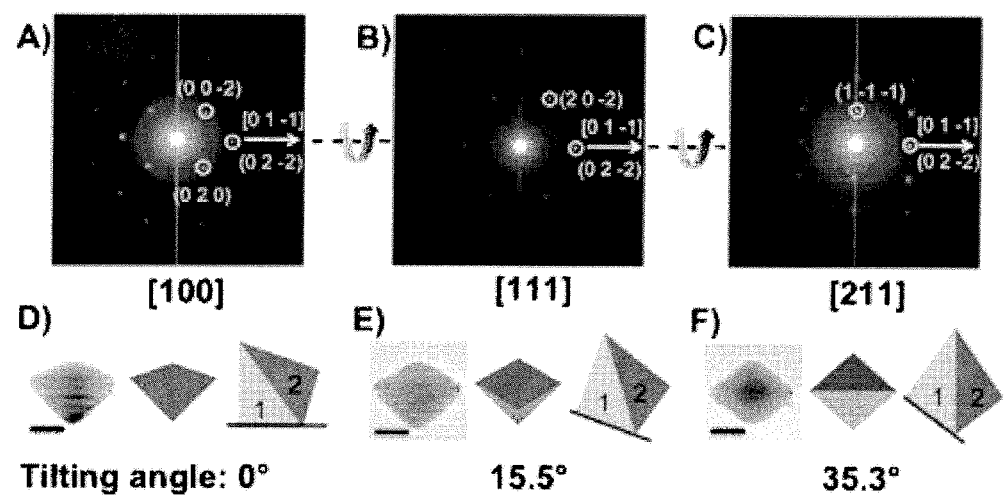
FIG. 7 shows A-C) tilted selected area electron diffraction (SAED) patterns of a single bipyramid at different incident angle between the electron beam and the crystal by tilting along the [0 1-1] direction; and D-F) tilted TEM images (scale bar 50 nm) and schematic illustrations of the top view and side view of the bipyramid at different incident angles, as indicated.

To confirm that the twinned nature of the bipyramid is preserved throughout the reaction, the final product was examined for twinned planes. HREM is not a suitable method for this experiment because of the large size of the final bipyramid structures. Instead, electron diffraction experiments were used to identify the twinned structure. A series of tilted selected area electron diffraction (SAED) patterns were collected by tilting one bipyramid inside an electron microscope (Hitachi HF-8100). With the double tilt holder, the relative orientation between incident electron beam and the crystal was altered. As shown in FIG. 7A, initially the crystal was tilted along the [100] zone axis, which was used as the zero point. When the crystal was tilted off the [100] zone by 15.5° and 35.3°, diffraction patterns were obtained which can be indexed as [111] and [211] zone axis respectively (FIGS. 7B and 7C). For a single face-centered cubic crystal, the smallest angle between [100] and [111] zone axes is 54.74°. The fact that a [111] diffraction pattern was obtained by tilting only 15.5° from the [100] zone axis implies that the bipyramid is a twinned crystal. Along with the diffraction patterns, TEM images were also collected for each orientation as shown in FIG. 7D-7F. Based on the tilted diffraction patterns and images, a model of the triangular bipyramid is proposed: the entire crystal is bisected by twinned (111) plane(s); the two twinning halves are denoted as 1 and 2 in FIG. 7. At an angle of 0°, the observed diffraction is dominantly part 1, since most lattice planes in part 1 satisfy the Bragg diffraction condition at this angle. At angle 15.5°, part 2 becomes the main contributor to the diffraction. However, when tilted to 35.3°, both twins are along the [211] zone axis. The experimental tilting angle between [100] and [211] zone axis of crystal 1 is 35.3°, and that between [211] and [111] zone axis of crystal 2 is 19.8°. Both tilt angles are very close to the theoretical values, 35.26° and 19.47°, respectively.

The results from HREM and electron diffraction experiment strongly indicate the twinning nature of seeds and the final products in bipyramid synthesis. To form bipyramids, the bisecting layer of the crystal must have an odd number of twin planes. This is the only possible way for a single crystal to evolve two halves with mirror symmetry, bisected by the minor plane. Although stacking faults happen throughout the whole crystal, they contribute negligibly final structure relative to the twinning nature of bipyramids because they discontinue but do not change the propagation direction of the crystal. More recently, right silver bipyramids were also observed as one of the products from the thermal overgrowth of silver platelets, which was attributed to the multiple planar twinned defects in the platelet seeds.[33]

Figure 8:
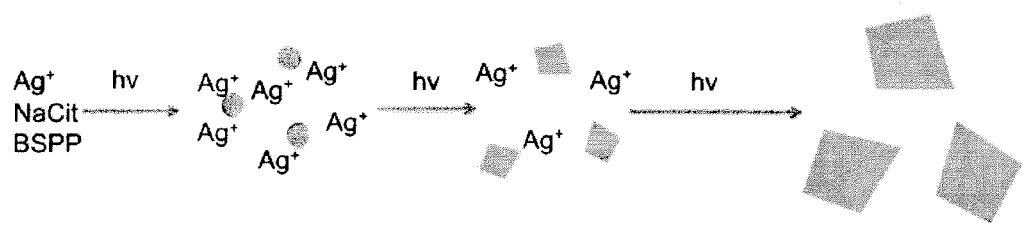
FIG. 8 shows a schematic illustration of the hypothesized mechanism for the formation of silver bipyramids.

Not wishing to be bound by theory, it is hypothesized that the bipyramids formed by the photoinduced method disclosed herein grow from a seed with an odd number of planar twinned defects (FIG. 8). Through plasmon excitation, these seeds enlarge and grow into small bipyramids, presumably with selective deposition on (111) facets, which eventually leads to their disappearance. This process is distinctly different from silver nanoprism synthesis, where the reduced silver atoms deposit only on the prism edges, leading to 2-D growth and {111} facets remain. The small bipyramids grow into bigger bipyramids through enlargement of their (100) facets, which is a plasmon-mediated process.

An efficient photoinduced synthesis for right triangular silver bipyramid nanoparticles with high yield is disclosed herein. By adjusting the excitation wavelength, the growth of monodisperse bipyramids with controllable edge lengths can be easily achieved. More importantly, the disclosed process provides an example of the control of the size and shape of nanoparticles through plasmon excitation, which is similar to earlier work with the triangular nanoprisms. It strongly suggests that plasmon resonance is an easier and more effective method of nano structure synthesis compared to the conventional wet chemistry methods.

The bipyramidal prisms disclosed herein can be used as new diagnostic labels, lighting up when target DNA is present. Biodetectors incorporating nanoprisms can be used to quickly, easily and accurately detect biological molecules as well as a wide range of genetic and pathogenic diseases, from genetic markers for cancer and neurodegenerative diseases to HIV and sexually transmitted diseases.

EXAMPLES

The present invention is further explained by the following examples which should not be construed by way of limiting the scope of the present invention.

Synthesis of Silver Right Triangular Bipyramids

Figure 9:
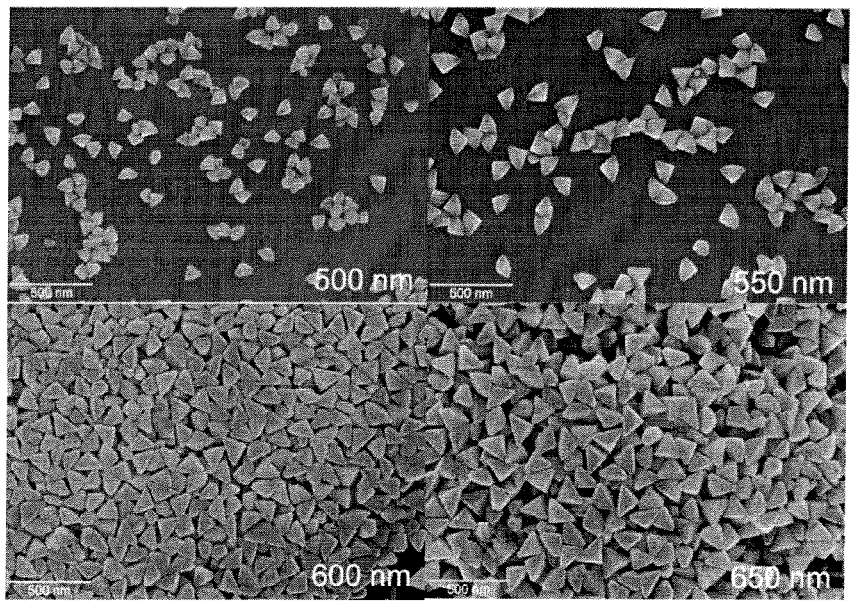
FIG. 9 shows wide-view (scale bar 500 nm) of SEM images of bipyramids obtained through irradiating at 500±20 nm, 550±20 nm, 600±20 nm, and 650±20 nm.
Figure 10:
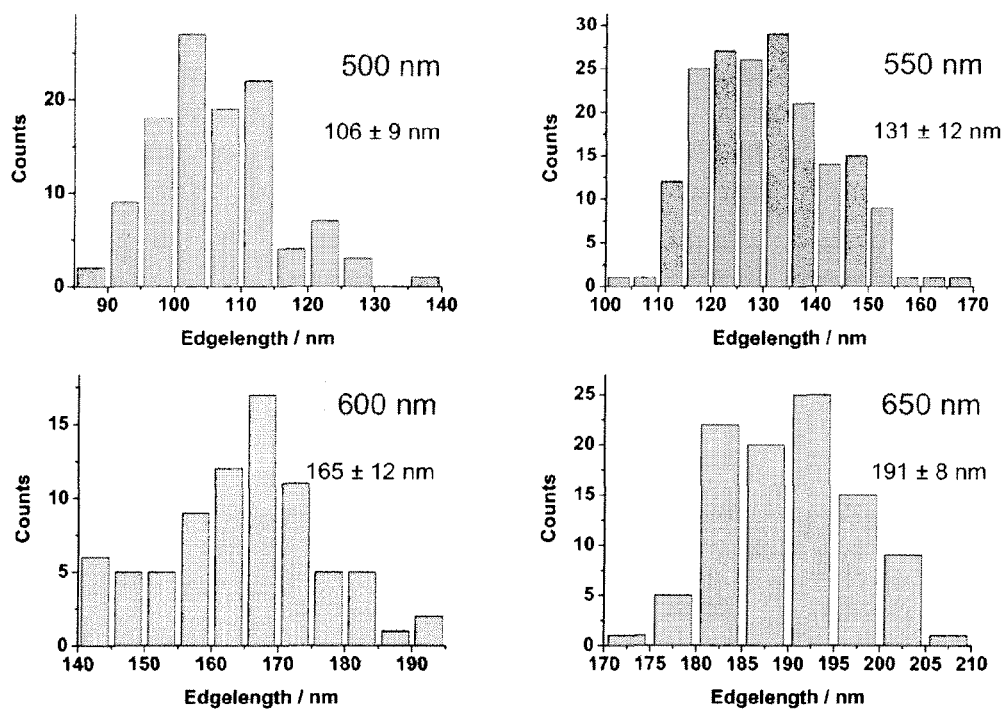
FIG. 10 shows statistical analyses of the edge length a of the triangular bipyramids obtained through irradiating at 500±20 nm, 550±20 nm, 600±20 nm, and 650±20 nm.

Nanopure water (18.5 mL), $AgNO_3$ (0.6 mL, 10 mM), BSPP (0.6 mL, 10 mM), sodium citrate (0.3 mL, 0.1 M) were mixed in a 24 mL vial. Then NaOH (1 mL, 0.1 M) was added into this mixture. The resulting solution was irradiated with a 150-W halogen lamp coupled with an optical bandpass filter (500±20 nm, 550±20 nm, or 600±20 nm). For the synthesis with a filter of 650±20 nm, the sample was first irradiated under 600±20 nm for one hour, and then switched to 650±20 nm for the rest of the synthesis. The distance between the lamp and filter was kept at 2 cm. The intensity of the lamp was varied from 0.3 W to 0.5 W, measured by an optical power meter (Newport 1916-C) coupled with a thermopile detector (818P-010-12) with an active diameter of 12 mm. SEM images of the resulting bipyramids are shown in FIG. 9. FIG. 10 shows statistical analyses of the resulting triangular bipyramids and their edge lengths.

All DDA calculations were carried out by DDSCAT7.0. [34] The grid spacing was 1 nm, and the refractive index of the medium was 1.331. The extinction spectra are orientation-averaged. For right bipyramids of 106 nm, 131 nm, 165 nm and 191 nm, the two transverse truncations are 20 nm, 30 nm, 0 nm and 0 nm, and the three longitudinal truncations are 20 nm, 20 nm, 20 nm and 25 nm, respectively.

The foregoing description is given for clearness of understanding only, and no unnecessary limitations should be understood therefrom, as modifications within the scope of the invention may be apparent to those having ordinary skill in the art.

What is claimed:

1. A method of preparing silver triangular bipyramids comprising
   irradiating a mixture comprising a silver salt, a reducing agent, a separation agent, and a base with light at a selected band of wavelengths for a time sufficient to form the silver triangular bipyramids having an a edge length and a b edge length,
   wherein the silver salt comprises a silver ion, the separation agent is present in a molar concentration of less or equal to the molar concentration of the silver ion, and the selected band of wavelengths of the light has a full width at half maximum (FWHM) of 50 nm or less.

2. The method of claim 1, providing at least 85% shape selectivity of triangular bipyramids.

3. The method of claim 2, wherein the shape selectivity is greater than 95%.

4. The method of claim 1, wherein the silver triangular bipyramids have a variation in the a or b edge length of less than 15%.

5. The method of claim 1, wherein the silver salt comprises silver nitrate.

6. The method of claim 1, wherein the separation agent comprises bis(p-sulphonatophenyl)phenylphosphine dehydrate dipotassium (BSPP).

7. The method of claim 1, wherein the reducing agent comprises citric acid or a salt thereof.

8. The method of claim 1, wherein the molar ratio of separation agent to silver ion is 1:1 to about 1:4.

9. The method of claim 1, wherein the mixture is irradiated at a band of wavelengths selected from the group consisting of 500±20 nm, 550±20 nm, 600±20 nm, and 650±20 nm.

10. The method of claim 1, wherein the light has a power intensity of about 0.1 to about 1 W.

11. The method of claim 10, wherein the light has a power intensity of about 0.3 to about 0.5 W.

12. The method of claim 1, wherein the mixture is irradiated for about 3 to about 8 hours.

13. The method of claim 1, wherein the mixture consists essentially of a silver salt, a reducing agent, a separation agent, and a base.

14. The method of claim 13, wherein the reducing agent is sodium citrate.

15. The method of claim 13, wherein the base is an inorganic base.

\* \* \* \* \*

UNITED STATES PATENT AND TRADEMARK OFFICE
CERTIFICATE OF CORRECTION

PATENT NO. : 8,425,653 B2  
APPLICATION NO. : 12/727483  
DATED : April 23, 2013  
INVENTOR(S) : Mirkin et al.

Page 1 of 1

It is certified that error appears in the above-identified patent and that said Letters Patent is hereby corrected as shown below:

In The Claims,

In Column 10, Line 12, in Claim 1, delete "less or" and insert -- less than or --, therefor.

Signed and Sealed this
Twenty-seventh Day of January, 2015

Michelle K. Lee
*Deputy Director of the United States Patent and Trademark Office*